United States Patent [19]
Freed et al.

[11] Patent Number: 5,833,655
[45] Date of Patent: Nov. 10, 1998

[54] PERCUTANEOUS ACCESS DEVICE HAVING REMOVABLE TURRET ASSEMBLY

[75] Inventors: Paul S. Freed, Bloomfield Hills; George Taro, Canton; Adrian Kantrowitz, Auburn Hills, all of Mich.

[73] Assignee: L. Vad Technology, Inc., Detroit, Mich.

[21] Appl. No.: 856,905

[22] Filed: May 15, 1997

[51] Int. Cl.⁶ .................................................. A61M 11/00
[52] U.S. Cl. ............................................. 604/93; 604/174
[58] Field of Search ........................... 604/93, 174, 175; 128/DIG. 26

[56] References Cited

U.S. PATENT DOCUMENTS

| | | |
|---|---|---|
| 3,826,241 | 7/1974 | Bucalo . |
| 4,004,298 | 11/1977 | Freed . |
| 4,321,914 | 3/1982 | Begovac et al. . |
| 4,393,873 | 7/1983 | Nawash et al. . |
| 4,579,120 | 4/1986 | MacGregor . |
| 4,581,020 | 4/1986 | Mittleman ............................... 604/175 |
| 4,630,597 | 12/1986 | Kantrowitz et al. . |
| 4,634,422 | 1/1987 | Kantrowitz et al. . |
| 4,790,826 | 12/1988 | Elftman .................................. 604/175 |
| 4,804,369 | 2/1989 | Lapeyre et al. ........................ 604/175 |
| 4,897,081 | 1/1990 | Poirier et al. . |
| 4,955,861 | 9/1990 | Enegren et al. ..................... 604/175 X |
| 5,098,397 | 3/1992 | Svensson et al. ...................... 907/175 |
| 5,139,508 | 8/1992 | Kantrowitz et al. . |
| 5,242,415 | 9/1993 | Kantrowitz et al. . |
| 5,312,364 | 5/1994 | Jacobs ................................. 604/174 X |
| 5,387,192 | 2/1995 | Glantz et al. ............................ 604/93 |
| 5,637,088 | 6/1997 | Wenner et al. .......................... 604/93 |

Primary Examiner—Manuel Mendez
Attorney, Agent, or Firm—Young & Basile, P.C.

[57] ABSTRACT

A percutaneous access device implantable beneath the skin of a patient which includes a housing having a flange positionable beneath the skin and neck projecting outward through the skin. The percutaneous access device includes electrical communication through the flange and fluid access through the flange. The components providing fluid access and electrical communication are removable through the neck portion of the implant for testing and service as required without the need for further surgery on the patient. A turret body is received within the hollow interior of the neck having a fluid channel extending therethrough and containing current limiting devices securely disposed within the turret body.

20 Claims, 2 Drawing Sheets

PERCUTANEOUS ACCESS DEVICE HAVING REMOVABLE TURRET ASSEMBLY

BACKGROUND OF THE INVENTION

I. Field of the Invention

This invention pertains to percutaneous access devices employed to establish a connection through the skin between an organ or device implanted within the human body and an external device such as a monitor, pump or the like. More particularly this invention pertains to percutaneous access devices having fluid and/or electrical conduits extending therethrough.

II. Description of Relevant Art

Various percutaneous devices have been employed to establish connection through the skin between an organ, or organ system, or an implanted device, and an external device. Various percutaneous access devices, hereinafter referred to as PADs, are surgically implanted through the skin of a patient for use on a long term basis. The devices provide both mechanical and electrical access to internal organs or devices. As such, these PADs can be equipped with channels for conveying fluid or gaseous material therethrough as well as various electrical contacts, current limiters and the like to provide electrical and electronic links between the internal organ to be monitored, or an internally implanted device, and the external devices such as monitors, pumps and the like.

Electrical contacts, current limiters and the like can, as well as mechanical devices, require periodic monitoring and maintenance. Heretofore, it has been customary to position current carrying electrical devices in the body of the PAD to provide greater clearance and access for other mechanical linkages, fluid, gaseous channels and the like. However, placement of electrical, and/or mechanical devices in the main body of the PAD housing complicates the task of performing routine diagnostics to ascertain the functioning and capability of the devices in the PAD. In addition, the fluid sealing surface on the PAD may become scratched or damaged requiring replacement to achieve the desired sealing characteristics. The connector supporting the fluid sealing surface ball may become cracked or break requiring replacement to reestablish an intact fluid conduit for the PAD. The electrical contacts may become corroded or oxidized resulting in bad electrical connections requiring service or replacement. Procedures for replacing failed or failing electrical or mechanical devices is complicated due to their location within the PAD housing. In many instances, surgical removal of the PAD is required to accomplish repair or replacement of an electrical or mechanical device.

Accordingly, it would be desirable to provide PADs having means for conveying electrical current and/or electronic data which are readily accessible. Additionally, it would be highly desirable to provide a PAD in which the electrical conveying devices can be easily removed from the PAD housing without disturbing the implanted PAD. Furthermore, it is also desirable to provide a PAD in which electrical conveying devices are assembled in a component package to provide easy and accurate removal and replacement of one component package for another. Finally, it is desirable to provide a PAD which is highly reliable and provides sufficient channels for conveyance of gaseous or liquid materials therethrough, while allowing disassembly, removal and/or replacement of mechanical parts requiring service without disturbing the implanted PAD or requiring surgery on the patient.

SUMMARY OF THE INVENTION

The percutaneous access device of the present invention includes a housing implantable within the patient and a turret assembly adapted to be removably fastened within the housing. The turret assembly contains at least one portion of a current conveying device which transfers current through the PAD to and from external sources. As embodied herein, the turret assembly includes at least one current limiting device as well as various contacts and mechanical mounting mechanisms adapted to matingly and positively attach to an externally located lead. The turret assembly also includes means for permitting the flow of fluid, such as a liquid or gaseous material, through the PAD to and from an externally attached device.

BRIEF DESCRIPTION OF THE DRAWINGS

The description herein makes reference to the accompanying drawings wherein like reference numerals refer to like parts throughout the several views, and wherein.

DESCRIPTION OF THE PREFERRED EMBODIMENT

Figure 1:
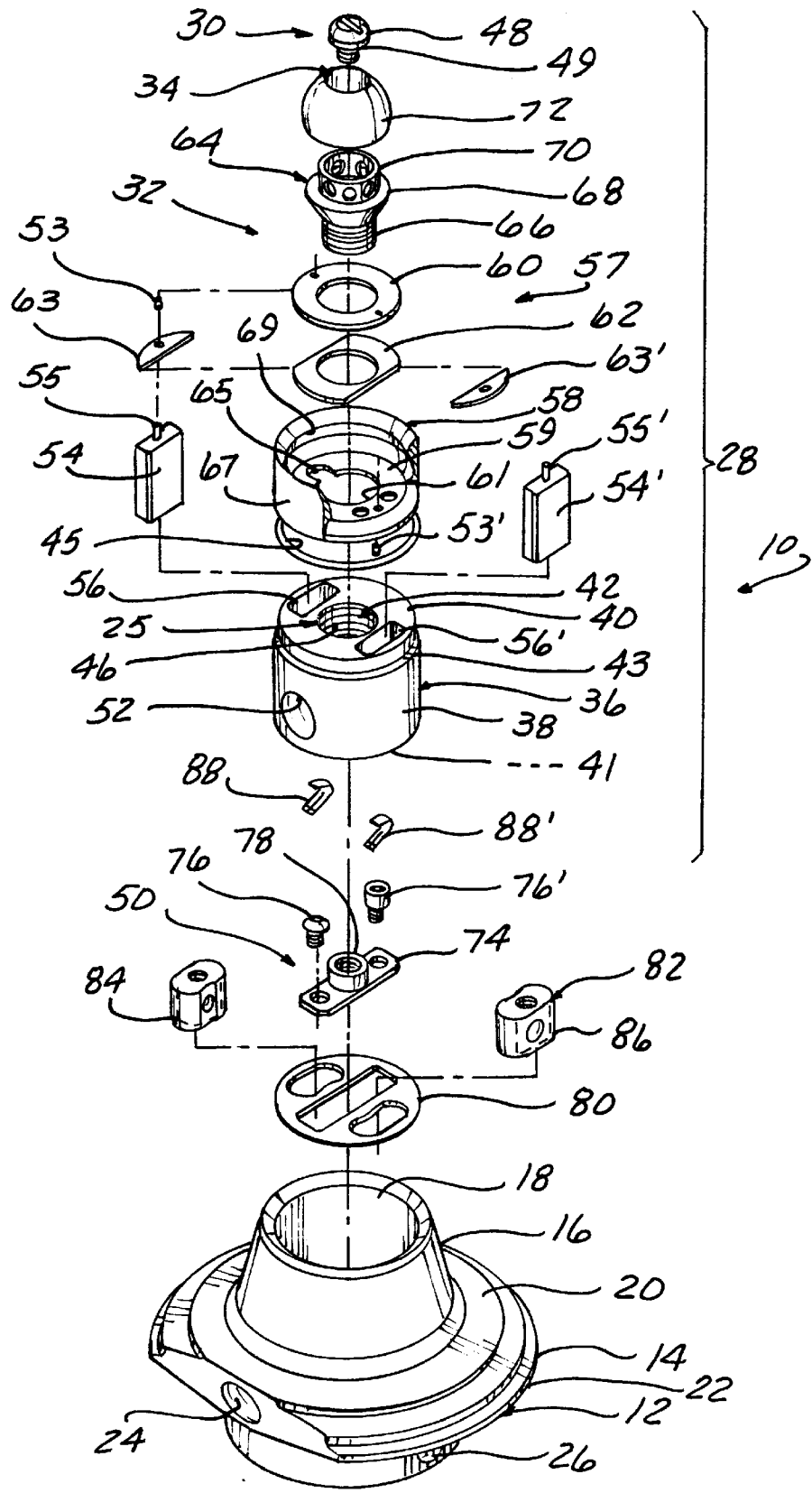
FIG. 1 is an exploded perspective view of the PAD device of the present invention including the implanted subassembly and the removable turret assembly.

The percutaneous access device (PAD) 10 of the present invention generally comprises a housing 12 and a removable turret assembly 28. The housing 12 is implantable beneath the skin of a patient in any suitable manner. Suitable techniques for implantation of PAD 10 are known to the skilled artisan and include but are not limited to the method described in U.S. Pat. No. 4,634,422, the specification of which is incorporated by reference herein. The general type of PAD may be employed, for example, to supply a pneumatic connection and electrocardiogram lead connections to a dynamic aortic patch of the type disclosed in Kantrowitz et al, U.S. Pat. No. 4,051,840. It will be understood, however, that the present invention is applicable to percutaneous access devices employed for other purposes. The housing 12 of the PAD 10 disclosed herein includes a flange body 14 which forms a main or base section. The housing 12 also includes a neck 16 which is integrally formed with the flange body 14 and projects outward therefrom. The neck 16 has a central passage defined therein which terminates in an end opening 18. The flange body 14 is generally a flat disc-shaped element having an upper wall 20 contiguous with the neck 16 and a lower wall 22 opposed to the upper wall and generally connected therewith. The housing 12 is composed of biologically non-reactive material which is suitable for implantation in a patient. Preferably, the housing 12 is implanted immediately below the dermal layer at the junction between the dermis and hypodermis. The inert material is generally an implantable medical grade polymeric material such as a polycarbonate. The outer surface of the housing 12 may have a textured, fibrous surface into which body tissues can grow and interlock.

Figure 3:
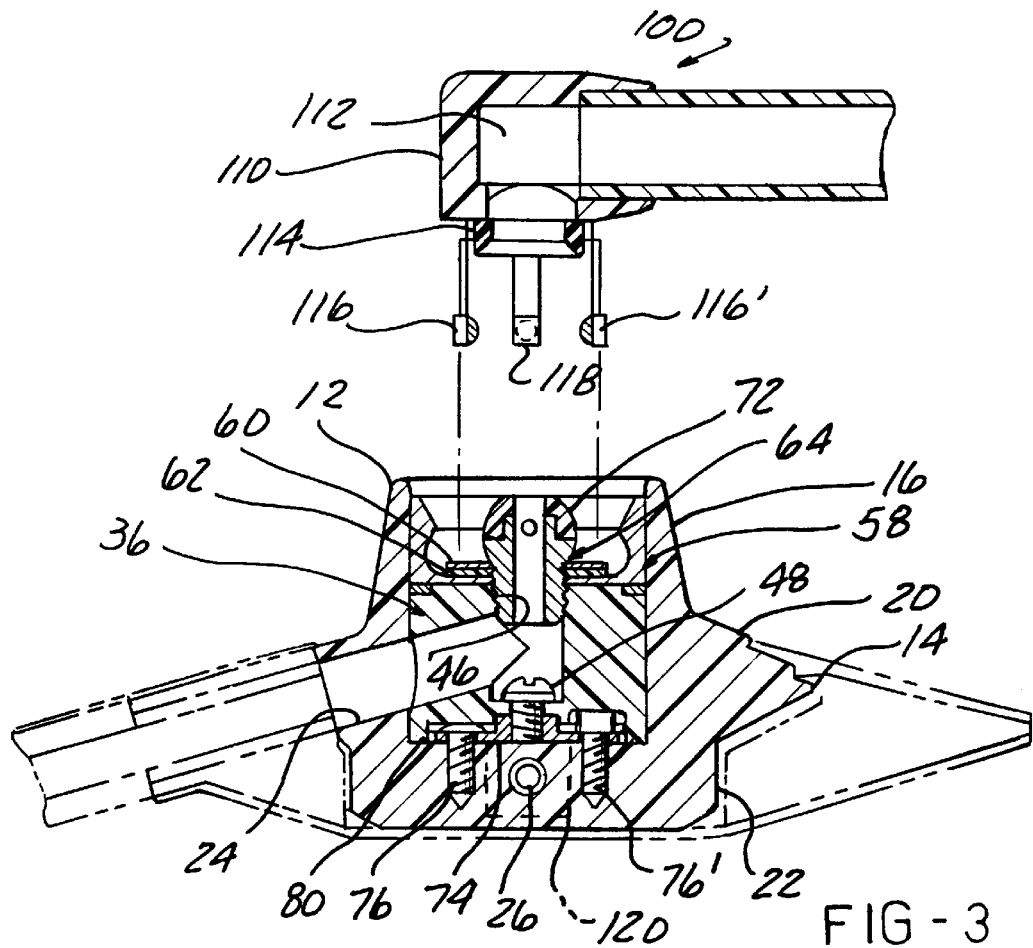
FIG. 3 is a cross-sectional view of the PAD device of the present invention.

The flange body 14 defines a central interior chamber seen in FIG. 3 including at least one fluid conveying channel which facilitates the transfer of fluid, such as a gaseous or liquid material, through the housing and terminates in an aperture 24 which is capable of providing communication between the exterior of the flange body 14 and the fluid conveying channel. As shown in the drawing figure, aperture 24 is located in lower wall 22. A suitable conduit (not shown) can be secured to the housing 12 at aperture 24 to provide communication between the corresponding fluid conveying channel in the flange body 14 and an associated device or organ. In instances in which the PAD is employed with a dynamic aortic patch, the specific conduit can convey gaseous material which controls the inflation and deflation of an associated aortic patch. However, it is to be understood that the material conveyed through such a conduit can be varied depending on the particular use desired for the PAD.

In the embodiment shown in the FIG. 1, an auxiliary aperture 26 and associated channel are also provided. This auxiliary aperture 26 and channel can provide access for various electronic monitoring leads, electrical wires or the like; i.e. for electrocardiogram monitoring leads, etc. Other apertures can be included in the flange body 14 as necessary.

The neck 16 of the housing 12 defines a hollow interior which communicates with the fluid channel defined in the flange body 14. The hollow interior is accessible through end opening 18. The hollow interior defined in the neck 16 is, preferably, essentially cylindrical and has a predefined internal diameter sufficient to receive a removable turret assembly 28.

The removable turret assembly 28 included in the PAD 10 of the present invention is adapted to matingly fit within the hollow interior defined by the neck 16 of the housing 12. The turret assembly 28 is removably fastened within the neck 16 by suitable means 30 for fastening turret assembly 28. The fastening means 30 is, preferably, at least partially contained within the flange body 14 of the housing 12 which will be described in greater detail subsequently.

The turret assembly 28 includes means 32 for providing electric communication through the housing 12 in a manner which provides insulation of the electrical current from communication and contact with body tissue surrounding the exterior of the housing. The turret assembly 28 also includes means 34 for providing fluid access to and communication to the fluid conveying channel in the flange body 14.

Figure 2:
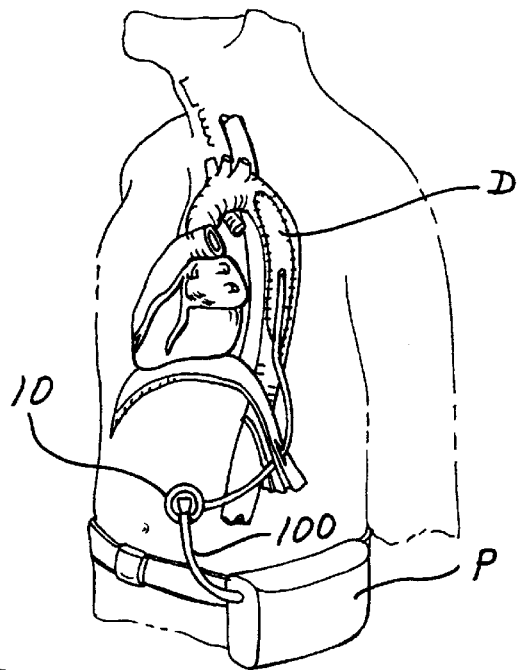
FIG. 2 is a schematic diagram illustrating the PAD device used in combination with an internally implanted device and an external monitoring/control device.

The turret assembly 28 includes a turret body 36 which has an outer surface configured to be received within the neck 16 of the housing 12. As shown in FIG. 1 and 2, the turret body 36 is an essentially cylindrical member having a cylindrical outer side surface 38, an upper outwardly facing surface 40, and an inwardly facing surface 41. The turret body 36 has a central shaft 42 which extends from an aperture located in the upper outwardly facing surface 40 into the central region of the turret body 36. The central shaft 42 is, preferably, positioned coaxially with the central longitudinal axis of the turret body 36. The central shaft 42 terminates at a blind inner wall located proximate to the lower inwardly facing surface 41 of the exterior of the turret body 36. A shaft extends through the blind inner wall to matingly receive a screw 48 sealed with a sealer or gasket 49. The screw 48 extends from the blind inner wall through the shaft and into threading engagement with suitable means 50 for securing the turret body 36 in the housing 12. Access to the screw 48 is provided through the aperture in the outwardly facing surface 40 and the associated central shaft 42. This provides the ability to remove and replace the turret assembly 28 as necessary.

The turret body 36 also includes a side shaft 52 extending from an opening in the outer cylindrical surface 38 to the central shaft 42 to provide a fluid channel 25 through the turret assembly 28. The position of the side shaft 52 in the turret body 36 permits the side shaft 52 to correspond to and communicate with the fluid conveying channel 25 defined in flange body 14 which corresponds to aperture 24 as depicted in FIG. 1. Thus, the fluid communication means 34 comprises a channel formed by the central shaft 42 and side shaft 52 which extend through the turret body 36 which provides communication from the upwardly facing surface of the turret body 36 through to the channel defined in the housing 12. The turret body 36 may include an annular groove 43 for receiving a seal 45, such as an O-ring seal to prevent migration of fluid from a position external of the patient to a position internal of the patient, and to prevent migration of body fluids from within the patient to a position external of the patient. The seal 45 also assists in isolating the fluid conduit from the electrical conduit in cooperation with gasket 80 and seal 49. The turret body 36 may be constructed of any suitable material which is durable and relatively light weight. Preferably, the material has electrical insulative characteristics. Examples of suitable materials include polyamide-imides and the like. Examples of polyamide-imides which are commercially available are TORLON available from Amoco Performance Products, Atlanta, GA. One suitable grade is TORLON 5030 POLYAMIDE-IMIDE with 30% Glass Fiber.

The turret assembly 28 also includes means for providing electrical communication to and from the flange body 14. The electrical communication means 32 includes at least one current limiting device 54 which is removably positioned within the turret body 36. Preferably, the electrical communication means 32, preferably, comprises a pair of current limiting devices 54, 54' which are received within corresponding compartments 56, 56' located in the turret body 36. The current limiting devices 54, 54' can be maintained in corresponding compartments 56, 56' by any suitable device, such as press fit contacts 53, 53' engaging corresponding lead 55, 55' respectively. In the embodiment shown in FIG. 1 and 3, the compartments 56, 56' are shafts extending through the turret body 36 configured to receive the associated current limiting device 54, 54' therein. As shown in FIGS. 1 and 3, the current limiting device 54, 54' sets within the associated compartments 56, 56' and are biased upwardly by engagement with corresponding spring contacts 88, 88' respectively. The spring contacts 88, 88' extend through end wall 41 of turret body 36 to engage corresponding kidney contacts 84, 86 respectively.

Lead 55' extends from the respective current limiting device 54' is engageable with a suitable ring contact 58 attached to the turret body 36 in overlying relationship to the upwardly facing surface 40. The electrical coupling assembly 57 also includes a suitable contact washer 60 overlying the face of the ring contact 58 with a suitable resilient insulator 62 interposed between and positioned coaxially to the ring contact 58 and contact washer 60 to provide two separate and independent electrical circuits or pathways. Fluid filter flaps 63, 63' prevent migration of body fluids from within the patient to a position external of the patient while allowing passage of evaporative gases that may form in the turret assembly 28.

As depicted in FIGS. 1 and 2, the current limiting devices 54, 54' may be any device which will provide regulated current to, from and through the PAD 10 of the present invention. Suitable current limiting devices incorporated in the implanted portion of the PAD preferably prevent passage of currents greater than 10 $\mu A$.

The ring contact 58 employed in the present invention includes a flat lower surface 59 having a central aperture 61 located therein. The flat lower surface 59 also includes means for providing electrical communication to and from the interior of the PAD 10. When a pair of current limiting devices are employed, the flat lower surface 59 of the ring contact 58 can include means for providing electrical communication between one current limiting device 54' and ring contact 58 (as shown in FIG. 1 at contact 53') and means for providing electrical communication of the other current limiting device 54 past the ring contact 58 directly to contact washer 60 (as shown in FIG. 1 at contact 53 passing through a curved extension 65 in central aperture 61). Contact washer 60 is electrically insulated from contact ring 58 by resilient insulation 62.

The ring contact 58 also includes an upwardly projecting annular member 67 having an inwardly projecting curved surface 69 projecting over the flat lower surface 59. The resilient insulator 62 and contact washer 60 overlay the flat lower surface 59 of ring contact 58 to provide a separate electrical path to contact surface 68 from the electrical path through the upwardly projecting annular member 67. The ring contact 58 and contact washer 60 are constructed of suitable conductive material such as stainless steel or the like. In situations where the PAD 10 of the present invention is employed for use with a dynamic aortic pump, the inwardly projecting surface 69 and contact surface 68 provide separate contacts for an electrocardiogram lead and the like.

In order to maintain the ring contact 58, contact washer 60 and insulator 62 in a position engaged with the turret body 36, the turret assembly 28 of the present invention also includes a suitable electrically conductive ball contact 64 adapted to be positioned in overlying relationship to the contact washer 60. The ball contact 64 has a threaded projection 66 adapted to be received in mating threaded engagement to an inner threaded surface 46 located on the upper portion on the central shaft 42 of the turret body 36. The ball contact 64 also includes a suitable contact surface 68 in overlying electrically conductive contact with the contact washer 60. An upwardly extended sleeve 70 is contiguously formed on the contact surface 68 to provide suitable contact between the ball contact 64 and an insulative ball cap 72. As depicted in FIGS. 1 and 3, the ball contact 64 includes a central shaft which extends from the upper sleeve 70 through the threaded projection 66 and provides communication to and through the channel defined in the turret body 36 by central shaft 42 and side shaft 52. The central shaft within ball contact 64 also provides an access means through the central shaft 42 for removing and/or fastening screw 48. Therefore, removal of the entire turret assembly 28 can be accomplished by removal of screw 48 through the channel defined by shaft 42 and the respective apertures located in the various ring contacts and contact washers. The turret assembly 28 can be removed from the implanted flange for maintenance and repair, or for replacement by a different turret assembly device. Access to the current limiting devices 54, 54' as well as to the various contact washers, ring contacts and the like is also readily available as these members are separable from the turret body 36 by unfastening ball contact 64.

In the embodiment shown in FIGS. 1 and 3, the turret assembly 28 also includes a suitable insulator ball cap 72 adapted to overlay the upper sleeve 70 of the ball contact 64. The insulator ball cap 72 can have any suitable surface which will facilitate mating contact between an external conduit device 100 and the PAD 10 of the present invention. As depicted in FIGS. 1 and 3, the insulator ball cap 72 is a hemispherical member overlying the upper sleeve and having a central shaft extending through the member in a manner coaxial with the shaft defined in the ball contact 64.

The ring contact 58, together with the ball contact 64 and insulative ball cap 72 provide a positive fastening mechanism for connection of external conduit device 100. The external conduit device 100 includes a connector member 110 having a fluid passage 112 extending therethrough which terminates at sealing gasket 114 adapted to matingly and sealingly contact the insulative ball cap 72 of the PAD 10 to provide fluid contact through the PAD 10 between the associated organ or device D and any external mechanisms or devices such as pump P.

As shown in FIG. 3, the external conduit device also includes a pair of electrically conductive fingers 116, 116' which project downward from the sealing gasket 114 to engage ball contact 64 along the contact surface 68, while a second pair (only one of which is shown in the cross-section of FIG. 3) 118 project downwardly from sealing gasket 114 to engage the ring contact 58 along an outer surface to convey electrical current to and from the PAD 10.

The turret assembly 28 can be fastened in the implantable housing 12 of the present invention by any suitable means, such as flange 74 and screw 48. As depicting in FIGS. 1 and 3, sealing screw 48 projects through the lower inwardly facing surface 41 of turret body 36 into suitable fastening contact with the lower wall 22 of flange body 14. While it is within the preview of this invention to secure screw 48 directly to the inner surface of lower wall 22, in order to provide secure engagement between the turret body 36 and the lower wall 22 of the flange body it is preferred that the housing 12 include suitable means 50 for removably fastening the turret body to the housing 12. As shown in FIGS. 1 and 3, the fastening means 50 includes a threaded flange device 74 secured to the inner face of the lower wall by a suitable mechanism such as cap screws 76, 76'. The threaded flange device 74 preferably has a central internally threaded projection 78 into which screw 48 is threadingly received. The inclusion of threaded flange device 74 in PAD 10 facilitates replacement and repair of the fastening means in the event of cross threading between the screw 48 and the internal threads of the projection 78 without requiring surgical removal of the entire PAD 10 from its implanted position in the body of the patient. The threaded flange device 74 may be constructed of any suitable durable material such as stainless steel or the like.

The threaded flange device 74 is preferably surrounded by a gasket 80 having an exterior diameter which corresponds to the internal diameter of the hollow opening in the neck 16. The gasket 80 is, preferably, constructed from a suitable compliant material such as silicone and surrounds the flange device 74 so as to fluidly isolate the electrical conduits and the fluid conduit. As depicted in FIG. 1, the gasket 80 also has a suitable opening for receiving at least one, and preferably two, wire terminal fittings 82 therethrough to be received in pockets 120 (FIG. 3) within the housing 12. The wire terminal fittings 82 are in electrical contact with internally extending leads (not shown). As depicted in FIG. 1, the wire terminal fittings include a large kidney contact 84 and a small kidney contact 86. The wire terminal fittings 82 are positioned in electrical contact with the current limiting device 54, 54' when the turret assembly 28 is in position in the housing 12. In order to facilitate this contact, the wire terminal fittings 82 can include suitable spring contacts 88, 88' located engaged with upwardly orientated faces of the kidney contacts 84, 86.

As shown in FIG. 1, the positioning of wire terminal fittings 82 corresponds to the openings in gasket 80. The wire terminal fittings 84, 86 are engageable within pockets or compartments 120 formed in the blind inner wall of central shaft 42 of housing 12 and are in electrical contact with current limiting devices 54, 54' through spring contacts 88, 88', respectively, extending into the compartments 56, 56' defined in the turret body 36, when the PAD 10 of the present invention is assembled. The upward projection of an enlarged head of one of the screws 76, 76' acting together with an enlarged slot or aperture in the bottom of turret 38 orients the side shaft 52 in fluid contact with the fluid conveying channel 25 of housing 12 during turret assembly 28 insertion operations. once turret assembly 28 is inserted in neck 16, screw 48 can be inserted through central shaft 42 and the apertures of the various components overlying the turret body and fastened in position.

Thus, the PAD 10 of the present invention permits removal of electricity conveying devices such as current limiters and the like for testing and replacement as necessary and various mechanical components. The PAD 10 of the present invention also combines electrical contacts, leads, current limiters and mechanical components in a single removable accessible unit without interfering with fluid flow through the device. Furthermore, the PAD 10 of the present invention provides a configuration in which electrical conveying devices are positively insulated from the outer housing. In addition, the fluid sealing surface on the PAD may become scratched or damaged requiring replacement to achieve the desired sealing characteristics. The connector supporting the fluid sealing surface ball may become cracked or break requiring replacement to reestablish an intact fluid conduit for the PAD. The electrical contacts may become corroded or oxidized resulting in bad electrical connections requiring service or replacement.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A percutaneous access device for implantation within a patient having at least a portion projecting outwardly through a skin of the patient comprising:

housing means for defining at least one chamber, the housing means having a flange portion positionable beneath the skin of the patient and an outwardly extending neck portion disposable passing through the skin of the patient;

at least one fluid conduit means and at least one electrical conduit means, each conduit means for communicating from an external position with respect to the patient to an internal position with respect to the patient, each of the conduit means passing through the neck portion and flange portion of the housing and in communication with the at least one chamber defined by the housing means; and means for externally removing at least a portion of each of the conduit means through the neck portion of the housing means.

2. The percutaneous access device of claim 1 wherein the means for externally removing further comprises:

a turret engageable through the neck to complementarily seat with respect to the chamber defined by the housing means.

3. The percutaneous access device of claim 2 wherein the turret further comprises:

means disposed within the turret for limiting current passing from the external position with respect to the patient to the internal position with respect to the patient.

4. A percutaneous access device for implantation within a patient having at least a portion projecting outwardly though a skin of the patient comprising:

housing means for defining at least one chamber, the housing means including a flange body having an upper wall orientatable toward the skin of the patient and a lower wall opposed to the upper wall, the upper and lower wall defining the at least one chamber in a central interior region, the flange body further having a first passage in communication between the at least one chamber in the central interior region and the exterior of the flange body, and a second passage extending external to the housing from the at least one chamber, a neck integrally formed with the upper wall of the flange body and projecting outward therefrom, the neck defining at least in part the chamber within the central interior region, the chamber having an internal surface, the neck terminating in an end region projectable above the outer surface of the skin of the patient, the end region having an outer end opening opposed to the lower wall of the flange body;

means for electrically communicating from a position external with respect to the patient to a position internal with respect to the patient, the electrical communicating means passing through the flange body and having at least one electrically conductive conduit associated therewith;

means for fluidly communicating from the position external with respect to the patient to the position internal with respect to the patient, the fluid communicating means passing through the interior region in the flange body and having at least one fluid conduit associated therewith; and means for removably positioning at least one of the fluid communicating means and the electrical communicating means within the housing means.

5. The percutaneous access device of claim 4 wherein the removable positioning means further comprises:

an elongated turret body matingly receivable within the neck, the turret body having an outer side surface, a central bore extending longitudinally therethrough, and a lateral bore extending from the outer side surface and terminating in communication with the central bore, the lateral bore positioned in the turret body in an orientation sufficient to provide fluid communication between the central bore and the fluid conduit located in the flange; and means for removably securing the turret body within the housing.

6. The percutaneous access device of claim 5 wherein the securing means further comprises:

a threaded screw sealingly engageable through an aperture located in an end of the turret body opposing the lower wall of the housing means; and a replaceable mounting flange locatable on the lower wall of the housing means, the mounting flange having an internally threaded aperture for matingly receiving the threaded screw therein.

7. The percutaneous access device of claim 4 wherein the electrical communicating means further comprises:

at least one wire terminal fitting maintained in position in the flange body of the housing means, the wire terminal fitting accessible through the outer end opening of the neck;

at least one means for limiting electrical current to the wire terminal fitting;

means for removably maintaining the current limiting means in position within the neck of the housing means; and at least one ring contact in removable contact with the current limiting means.

8. The percutaneous access device of claim 7 wherein the removable maintaining means further comprises:

a turret body constructed of an electrically insulating material, the turret body matingly received with respect to the internal surface of the neck, the turret body having an outer side surface engageable with the internal surface of the neck and having an end surface opposing the lower wall of the flange body of the housing means, the turret body further defining a sleeve having pockets to removably receive the current limiting means therein; and a threaded screw engageable through the end wall of the turret body and releasably connectible with the lower wall of the housing means.

9. The percutaneous access device of claim 7 further comprising:

a spring contact interposed between the wire terminating fitting and flexibly contacting the current limiting means;

a replaceable mounting flange connectible to the lower wall of the flange body of the housing means, the mounting flange having a internally threaded aperture adapted to matingly receive the threaded screw therein; and a gasket disposed between the lower wall of the flange body of the housing means and the turret body to seal the fluid communicating means, the gasket generally coplanar with and extending outward from the mounting flange, the gasket having an opening conforming to allow electrical connection of said electrical current limiting means to the wire terminating fitting.

10. The percutaneous access device of claim 7 wherein the electrical communicating means further comprises:

a resilient insulator having a central aperture, the resilient insulator in overlying contact with the ring contact, the aperture of the resilient insulator essentially coaxial with respect to the aperture of the ring contact;

an electrically conductive contact washer having a central aperture, the contact washer overlying the resilient insulator with the respective apertures coaxially disposed;

an electrically conductive ball contact disposed within and projecting outward from the respective apertures in the ring contact, resilient insulator and the contact washer; and an insulative ball cap disposed over the electrically conductive ball contact, the insulative ball cap having at least one opening providing access to the ball contact.

11. A percutaneous access device for implantation within a patient having at least a portion projecting outwardly through a skin of the patient comprising:

a housing for implantation beneath the skin of the patient such that a portion of the housing projects outwardly though the skin, the outwardly projecting portion defining an interior region and an opening providing access thereto, the opening located in the outwardly projecting portion of the housing;

a turret subassembly removably contained in the housing, the turret subassembly removable through the opening in the outwardly projecting portion of the housing subassembly; and at least one fluid conduit means and at least one electrical conduit means, each conduit means for communicating from an external position with respect to the patient to an internal position with respect to the patient, each of the conduit means passing through the turret subassembly and the housing.

12. A percutaneous access device for implantation within a patient having at least a portion projecting outwardly through a skin of the patient comprising:

a housing for implantation beneath the skin of the patient such that a portion of the housing projects outwardly though the skin, the outwardly protecting portion defining an interior region and an opening providing access thereto, the opening located in the outwardly projecting portion of the housing; and a turret subassembly removably contained in the housing, the turret subassembly removable through the opening in the outwardly projecting portion of the housing subassembly, wherein the turret subassembly further comprises:

a turret body constructed of an electrically insulative material, the turret body having an upper face, a lower face, an internally threaded central shaft extending inward from the upper face, and at least one current limiter compartment;

means for limiting electrical current passing through the percutaneous access device from a position external with respect to the patient to a position internal with respect to the patient, the current limiting means contained within the current limiter compartment, the current limiting means having at least one lead extending outward from the current limiter compartment; and an electrically conductive ball contact having an outwardly threaded extension, the outwardly threaded extension threadingly receivable within the internally threaded central shaft in the turret body.

13. The percutaneous access device of claim 12 wherein the turret subassembly further comprises:

an electrically conductive contact ring overlying the upper face of the turret body and interposed between the turret body and the ball contact, the contact ring having a central opening, the central opening coaxially positioned relative to the threaded central shaft in the turret body;

a resilient insulator having a central opening, the central opening coaxially positioned relative to the threaded central shaft in the turret body;

an electrically conductive contact washer interposed between the ball contact and the resilient insulator, the electrically conductive contact washer coaxially positioned relative to the contact ring and insulator.

14. The percutaneous access device of claim 13 further comprising:

the turret body having a laterally extending bore positioned in the turret body in an orientation sufficient to provide gaseous fluid communication between the threaded central bore and an aperture located in the housing means; and means for removably securing the turret body in the housing means.

15. The percutaneous access device of claim 14 wherein the removable securing means further comprises:

a threaded screw engageable through the lower face of the turret body and removably secured to an inner surface of the housing means.

16. A percutaneous access for implantation within a patient having at least a portion projecting outwardly through a skin of the patient comprising:

a housing for implantation beneath the skin of the patient such that a portion of the housing projects outwardly though the skin, the outwardly projecting portion defining an interior region and an opening providing access thereto, the opening located in the outwardly projecting portion of the housing wherein the housing means further comprises:

a flange body implantable beneath the skin of a patient, the flange body having an upper wall adapted to be oriented toward the skin of the patient and a lower wall opposed to the upper wall, the upper and lower wall defining a chamber in a central interior region, the flange body further having a first passage communicating between the chamber and a position internal with respect to the patient, and a second passage communicating between the chamber and a position external with respect to the patient;

a neck integrally formed with the upper wall of the flange body and projecting outward therefrom, the neck having an essentially hollow interior with an essentially uniform inner diameter, the neck terminating in an end region, the neck having sufficient height to project the end region above the outer surface of the skin of the patient when the housing means is implanted therein, the end region having an outer end opening opposed to the lower wall of the flange body; and a turret subassembly removably contained in the housing, the turret subassembly removable through the opening in the outwardly projecting portion of the housing subassembly.

17. The percutaneous access device of claim 16 wherein the housing means further comprises:

at least one wire terminal fitting maintained in position in the flange body of the housing, the wire terminal fitting accessible through the outer end opening of the neck;

an interior flange mounted on the lower wall of the flange body of the implantable housing means, the interior flange including means for removably securing the turret subassembly thereto; and a gasket in contact with the lower wall of the flange body of the housing subassembly, the gasket coplanar with and extending outward from the interior flange, the gasket having an opening conforming to the lower wall and receiving the wire terminal fitting.

18. The percutaneous access device of claim 3 wherein the current limiting means further comprises:

at least one current limiter operably disposed in electrical communication with current passing through the electrical conduit means, the current limiter removable with the turret for maintenance and testing.

19. The percutaneous access device of claim 11 wherein the turret subassembly further comprises:

means disposed within the turret subassembly for limiting current passing through the electrical conduit means from the external position with respect to the patient to the internal position with respect to the patient.

20. The percutaneous access device of claim 19 wherein the current limiting means further comprises:

at least one current limiter operably disposed in electrical communication with current passing through the electrical conduit means, the current limiter removable with the turret subassembly for maintenance and testing.

* * * * *